United States Patent
Watanabe et al.

(10) Patent No.: US 6,184,230 B1
(45) Date of Patent: Feb. 6, 2001

(54) ANTI-*HELICOBACTER PYLORI* PHARMACEUTICAL COMPOSITION

(75) Inventors: Masato Watanabe; Kouichi Tanaka; Masayuki Komiya, all of Tokyo (JP); Ratna Murni Rantiatmodjo, Jakarta (ID)

(73) Assignees: Yamanouchi Pharmaceutical Co., Ltd., Tokyo (JP); P. T. Kalbe Farma, Jakarta Timur (ID)

( * ) Notice: Under 35 U.S.C. 154(b), the term of this patent shall be extended for 0 days.

(21) Appl. No.: 09/423,924
(22) PCT Filed: May 14, 1998
(86) PCT No.: PCT/JP98/02133
§ 371 Date: Nov. 16, 1999
§ 102(e) Date: Nov. 16, 1999
(87) PCT Pub. No.: WO98/51306
PCT Pub. Date: Nov. 19, 1998

(30) Foreign Application Priority Data

May 16, 1997 (JP) .................................................. 9-127462

(51) Int. Cl.[7] .................................................. A61K 31/47
(52) U.S. Cl. .............................................................. 514/311
(58) Field of Search ............................................... 514/311

(56) References Cited

PUBLICATIONS

Kamigiri et al, Chemical Abstracts, vol. 125, No. 216507t. 1996.*

\* cited by examiner

*Primary Examiner*—James H. Reamer
(74) *Attorney, Agent, or Firm*—Sughrue, Mion, Zinn, Macpeak & Seas, PLLC

(57) ABSTRACT

An anti-*Helicobacter pylori* pharmaceutical composition containing a 1-hydroxy-3-methyl-quinolone derivative represented by the following formula (I)

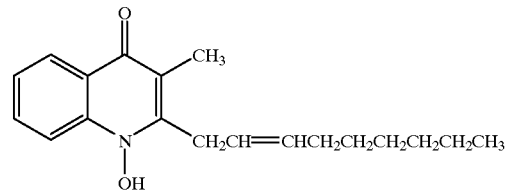

or a pharmaceutically acceptable salt thereof as an active ingredient.

Since it shows antibacterial action upon *Helicobacter pylori*, this invention is effective for the treatment or prevention of infection with *Helicobacter pylori* in human and infection with related bacteria belonging to the genus Helicobacter in animals. Also, the anti-*Helicobacter pylori* pharmaceutical composition of the present invention is useful for the prevention (including prevention of relapse) or treatment of diseases of the upper digestive organs, such as peptic ulcers (e.g., gastric and duodenal ulcers), inflammations (e.g., acute or chronic gastritis or duodenitis) and gastric cancer, as well as MALT (mucosa-associated lymphoid tissue) lymphoma or chronic heart diseases.

4 Claims, No Drawings

ANTI-*HELICOBACTER PYLORI* PHARMACEUTICAL COMPOSITION

TECHNICAL FIELD

This invention relates to a medicament, particularly an anti-*Helicobacter pylori* pharmaceutical composition. In particular, it relates to an anti-*Helicobacter pylori* agent which is useful for the treatment and prevention of various diseases caused by the infection with *Helicobacter pylori*.

BACKGROUND ART

*Helicobacter pylori* is a pathogenic bacterium discovered in 1983, which is regarded as the cause of diseases at the upper digestive organs, such as peptic ulcers (e.g., gastric and duodenal ulcers), inflammations (e.g., gastritis) and gastric cancer, and of MALT (mucosa-associated lymphoid tissue) lymphoma or as a background pathogenic factor of chronic heart diseases. Studies on the treatment of *Helicobacter pylori* infection are active now, and a large number of therapeutic methods have been reported, including those for removing the bacterium or those for preventing relapse, as described below. The examples include a single agent administration method using bismuth, an antibiotic, a proton pump inhibitor (PPI), an antitumor agent, or the like and a multiple agent combination method (two agent combination or three agent combination) which uses a combination of these agents, etc. ("Internal Medicine", Special Edition, vol. 78, no. 1 (1996), published by Nankodo). However, these therapeutic methods have many problems to be solved, such as high frequency of administration times, requirement of administration in a dose larger than the usual dose in some cases, onset of diarrhea or constipation caused by the drug administration and generation of resistant strains.

The compound related to the present invention as a substance useful as an anti-*Helicobacter pylori* pharmaceutical composition, is disclosed in JP-A-7-189 (the term "JP-A" as used herein means an "unexamined published Japanese patent application") as a substance YL-02729S, and its use is particularly antibacterial activity upon methicillin-resistant *Staphylococcus aureus*. Said patent application does not suggest or report about antibacterial activity of the substance YL-02729S upon *Helicobacter pylori*.

DISCLOSURE OF THE INVENTION

The inventors of the present invention have carried out extensive studies on the aforementioned substance YL-02729S and, as a result, found that it has an excellent anti-*Helicobacter pylori* activity and also that said substance has high selectivity and does not exert influences upon other bacteria.

The following describes the present invention in detail.

The present invention relates to an anti-*Helicobacter pylori* pharmaceutical composition containing a 1-hydroxy-3-methyl-quinolone derivative represented by the following formula (I)

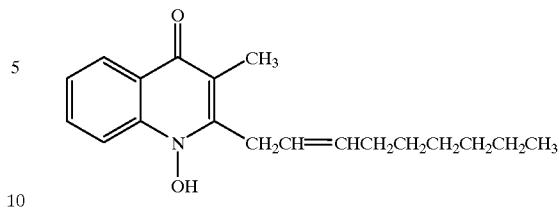

or a pharmaceutically acceptable salt thereof as an active ingredient, preferably an anti-*Helicobacter pylori* pharmaceutical composition containing 1-hydroxy-2-(2-trans-nonenyl)-3-methyl-4(1H)-quinolone or a pharmaceutically acceptable salt thereof as an active ingredient, and to the use of a 1-hydroxy-3-methyl-quinolone derivative represented by the following formula (I)

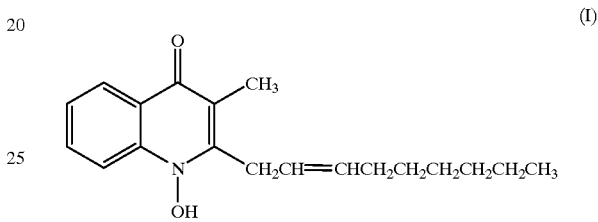

or a pharmaceutically acceptable salt thereof for the production of an anti-*Helicobacter pylori* agent.

The present invention also relates to the use of an anti-*Helicobacter pylori* pharmaceutical composition containing a 1-hydroxy-3-methyl-quinolone derivative represented by the formula (I) or a pharmaceutically acceptable salt thereof as an active ingredient for the prevention or treatment of *Helicobacter pylori* infection, to a method for the administration of the substance of formula (I) and other agent, preferably an antibiotic, an acid-related agent or an H2 blocker, simultaneously or at an interval and to the use thereof for the prevention of relapse of diseases caused by *Helicobacter pylori* infection. Also included in the present invention is a prodrug of the substance of formula (I) obtained by a usual means.

Since the active ingredient (I) of the anti-*Helicobacter pylori* pharmaceutical composition of the present invention has double bonds, cis isomer and trans isomer, as well as tautomers exist therein. Existence of the tautomers is disclosed in JP-A-7-189 as follows.

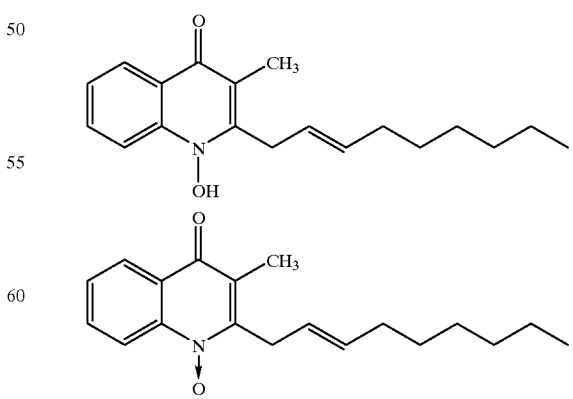

Examples of the pharmaceutically acceptable salt include acid addition salts with inorganic acids or organic acids, of which pharmaceutically acceptable salts are desirable. Illustrative examples of such salts include acid addition salts with mineral acids such as hydrochloric acid, hydrobromic acid, hydroiodic acid, sulfuric acid, nitric acid and phosphoric acid, with organic acids such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid or with acidic amino acids such as aspartic acid and glutamic acid. Hydrates and various solvates of the active ingredient are also included in the present invention. Also, said active ingredient exists in polymorphic forms in some cases, and all of such crystal forms are included in the present invention.

The production method disclosed in JP-A-7-189 can be cited as a typical method for the production of the active ingredient of the anti-*Helicobacter pylori* pharmaceutical composition of the present invention. Regarding a fermentation method for the production of said active ingredient, it is desirable to employ a method in which a bacterium belonging to the genus Arthrobacter, such as Arthrobacter sp. YL-02729S which has been deposited in National Institute of Bioscience and Human Technology under an international deposition No. FERM BP-6326, is cultured, and the compound of interest is isolated and purified from said culture in the usual way.

INDUSTRIAL APPLICABILITY

Since the invention compound shows antibacterial action upon *Helicobacter pylori*, the present invention is effective for the treatment or prevention of bacterial infection with *Helicobacter pylori* in human and with related bacteria belonging to the genus Helicobacter in animals. Also, the anti-*Helicobacter pylori* pharmaceutical composition of the present invention is useful for the prevention (including prevention of relapse) or treatment of diseases of the upper digestive organs, such as peptic ulcers (e.g., gastric and duodenal ulcers), inflammations (e.g., acute or chronic gastritis or duodenitis) and gastric cancer, as well as MALT (mucosa-associated lymphoid tissue) lymphoma or chronic heart diseases.

Preparation method and administration method of the anti-*Helicobacter pylori* pharmaceutical composition of the present invention are described in the following in detail.

The pharmaceutical composition containing one or more of the substance represented by the aforementioned formula (I) and pharmaceutically acceptable salts thereof as an active ingredients is administered orally or parenterally by preparing it into dosage forms such as tablets, powders, fine granules, granules, capsules, pills, solutions, injections, suppositories, ointments or adhesive preparations using generally used carriers, fillers and other additives for pharmaceutical preparation use.

Clinical dose of the present invention for human is optionally decided by taking into consideration symptoms, body weight, age, sex and other conditions of each patient to be treated.

The dose is generally from 0.1 to 500 mg in the case of oral administration, or from 0.01 to 100 mg in the case of parenteral administration, per day per adult, and the daily dose is divided into 1 to several doses per day. Since the dose varies depending on various conditions, a smaller amount than the above range may be sufficient in some cases. In this connection, the anti-*Helicobacter pylori* pharmaceutical composition of the present invention can be used in combination with other drugs such as antibacterial agents which will be described later, simultaneously or at an interval.

The solid composition of the present invention for use in oral administration is used in the form, for example, of tablets, powders or granules. In such a solid composition, one or more of the active substances are mixed with at least one inert diluent such as lactose, mannitol, glucose, hydroxypropylcellulose, microcrystalline cellulose, starch, polyvinyl pyrrolidone, metasilicate or magnesium aluminate. In addition to the inert diluent, the composition may contain other additives in the usual way, which include a lubricant such as magnesium stearate, a disintegrating agent such as calcium cellulose glycolate, a stabilizer such as lactose and a solubilizing or solubilization assisting agent such as glutamic acid or aspartic acid. As occasion demands, tablets or pills may be coated with a film of a gastric or enteric substance such as sucrose, gelatin, hydroxypropylcellulose or hydroxypropylmethylcellulose phthalate.

The liquid composition for oral administration use includes pharmaceutically acceptable emulsions, solutions, suspensions, syrups, elixirs and the like preparations and contains a generally used inert diluent such as purified water or ethyl alcohol. In addition to the inert diluent, this composition may also contain a solubilizing or solubilization assisting agent, a moistening agent, a suspending agent and the like auxiliary agents, as well as sweeteners, flavors, aromatics and antiseptics.

The injections for parenteral administration use include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohol (e.g., ethyl alcohol), polysorbate 80 (trade name, polyoxyethylene sorbitan higher fatty acid ester). Such a composition may further contain additive agents such as a tonicity agent, an antiseptic, a moistening agent, an emulsifying agent, a dispersing agent, a stabilizing agent (e.g., lactose) and a solubilizing or solubilization assisting agent. These preparations are sterilized for example by filtration through a bacteria retaining filter, blending of a germicide or irradiation. Alternatively, they may be used by firstly making into sterile solid compositions and dissolving them in sterile water or a sterile solvent for injection use prior to their use.

When the compound of the present invention has low solubility, it may be subjected to a solubilization treatment. The solubilization treatment may be effected by known methods which can be applied to pharmaceutical preparations, such as a method in which surface active agents (e.g., polyoxyethylene hardened castor oils, polyoxyethylene sorbitan higher fatty acid esters, polyoxyethylene polyoxypropylene glycols or sucrose fatty acid esters) are added, and a method in which a drug is formed into solid dispersion together with a solubilizing agent such as a high polymer (hydroxypropylmethylcellulose (HPMC), polyvinyl pyrrolidone (PVP), polyethylene glycol (PEG) or the like water-soluble high polymer or carboxymethylethylcellulose (CMEC), hydroxypropylmethylcellulose phthalate (HPMCP), methyl methacrylate-methacrylic acid copolymer (Eudragit L, S, trade name, manufactured by Rohm & Haas) or the like enteric high polymer). In addition, as occasion demands, a method in which the drug is made into a soluble salt or a method in which an inclusion compound is formed using cyclodextrins such as (α-cyclodextrin, β-cyclodextrin, γ-cyclodextrin, hydroxypropyl β-cyclodextrin or the like hydroxyalkylated cyclodextrin, methylated cyclodextrin or dimethyl β-cyclodextrin or dextrins may also be employed. The solubilization means can be optionally changed depending on each drug of interest ["*Recent Preparation Techniques and Their Application*", I. Utsumi et al., "*Drug Journal*", 157–159 (1983) and "*Pharmacology Monograph No. 1, Bioavailability*", K. Nagai et al., published by Soft Science, 78–82 (1988)]. Among the above techniques, a method in which solubility of a drug is improved by forming its solid dispersion with a solubilizing agent (JP-A-56-49314, FR 2460667) may be employed preferably.

According to the present invention, the aforementioned active compound can be used not only alone but in combination with other antibacterial agents (preferably 1 to 3 agents).

As described in the foregoing, such agents can be used jointly with the anti-*Helicobacter pylori* pharmaceutical composition of the present invention, simultaneously or at an interval. Examples of such other antibacterial agents include nitroimidazole antibiotics (e.g., tinidazole and metronidazole), tetracycline drugs (e.g., tetracycline, minocycline or doxycycline), penicillin drugs (e.g., amoxicillin, ampicillin, talampicillin, bacampicillin, lenampicillin, mezlocillin and sultamicillin), cephalosporin drugs (e.g., cefaclor, cefadroxil, cefalexin, cefpodoxime proxetil, cefixime, cefdinir, ceftibuten, cefotiam hexetyl, cefetamet pivoxil or cefuroxime axetil), penem drugs (e.g., faropenem or ritipenem acoxil), macrolide drugs (e.g., erythromycin, oleandomycin, josamycin, midecamycin, rokitamycin, clarithromycin, roxithromycin or azithromycin), lincomycin drugs (e.g., lincomycin or clindamycin), aminoglycoside drugs (e.g., paromomycin), quinolone drugs (e.g., ofloxacin, levofloxacin, norfloxacin, enoxacin, ciprofloxacin, lomefloxacin, tosufloxacin, fleroxacin, sparfloxacin, temafloxacin, nadifloxacin, grepafloxacin or pazufloxacin) and nitrofurantoin. In addition, a combination of the aforementioned active compound with a medicinal compound to be used in the treatment of acid-related diseases {e.g., an acid pump inhibitor (e.g., omeprazole or lansoprazole)}, an H2 antagonist (e.g., ranitidine, cimetidine or famotidine) or a gastric mucosa protecting agent which has an action to inhibit adhesion of *Helicobacter pylori* to gastric mucosa is also included within the scope of the present invention.

BEST MODE OF CARRYING OUT THE INVENTION

Examples of the present invention are given below by way of illustration and not by way of limitation.

EXAMPLE 1

An in vitro test of the invention substance was carried out in the following manner. Measurement of antibacterial activity (1) Preparation of antibacterial substance-containing agar plate The substance to be evaluated was dissolved in 100% dimethyl sulfoxide (DMSO) and diluted by 2-fold serial dilution. Each of the dilution solutions was put into a sterilized round Petri dish and mixed with 10 ml of Brucella agar medium (0.1% β-cyclodextrin) which had been sterilized and kept at 50° C., and the mixture was solidified. Final concentration of DMSO becomes 1% or less.

(2) Preparation of inoculation material and judgment of test results

A *Helicobacter pylori* strain, for example *Helicobacter pylori* ATCC 43504, was cultured at 37° C. for 3 days in a multi gas incubator ($N_2$: 80%, $CO_2$: 15%, $O_{2,\ 5}$%) using Brucella agar medium (containing 5% calf serum) and then prepared into a cell suspension of about $10^8$ cells/1 ml using Brucella broth based on its turbidity. The cell suspension was diluted 100 times with Brucella broth, and about 5 μl portion of the dilution was inoculated onto the surface of the drug-containing agar medium using a microplanter. The thus inoculated agar plate was cultured at 37° C. for 3 days (72 hours) in the aforementioned multi gas incubator. After completion of the culturing, the agar plate was observed, and the minimum drug concentration by which cell growth was not observed was defined as MIC. As the result, MIC of the *Helicobacter pylori* pharmaceutical composition of the present invention was found to be 0.025 μg/ml.

EXAMPLE 2

An in vitro test of the aforementioned substance was carried out in the following manner.

Measurement of antibacterial activity

Preparation of Antibacterial Substance-containing Agar Plate

The substance to be evaluated was dissolved in 100% dimethyl sulfoxide (DMSO) and diluted by 2-fold serial dilution. Each of the dilution solutions was put into a sterilized round Petri dish and mixed with 10 ml of Brucella agar medium (0.1% β-cyclodextrin) which had been sterilized and kept at 50° C., and the mixture was solidified. Final concentration of DMSO becomes 1% or less.

Preparation of Inoculation Material and Judgment of Test Results

A *Helicobacter pylori* strain, for example *Helicobacter pylori* ATCC 43504, was cultured at 37° C. for 3 days in a multi gas incubator ($N_2$: 80%, $CO_2$: 15%, $O_{2,\ 5}$%) using Brucella agar medium (containing 5% calf serum albumin) and then prepared into a cell suspension of about $10^8$ cells/1 ml using Brucella broth based on its turbidity. The cell suspension was diluted 100 times with Brucella broth, and about 5 μl portion of the dilution was inoculated onto the surface of the drug-containing agar medium using a microplanter. The thus inoculated agar plate was cultured at 37° C. for 3 days (72 hours) in the aforementioned multi gas incubator. After completion of the culturing, the agar plate was observed, and the minimum drug concentration by which cell growth was not observed was defined as MIC. As the result, MIC of 1-hydroxy-2-(2-trans-nonenyl)-3-methyl-4(1H)-quinolone was found to be 0.025 μg/ml.

EXAMPLE 3

An in vitro test on facultative anaerobes and aerobes was carried out in the following manner.

Preparation of Antibacterial Substance-containing Agar Plate

The substance to be evaluated was dissolved in 100% dimethyl sulfoxide (DMSO) and diluted by 2-fold serial dilution. Each of the dilution solutions was put into a sterilized round Petri dish and mixed with 10 ml of Muller-Hinton agar medium which had been sterilized and kept at 50° C., and the mixture was solidified. Final concentration of DMSO becomes 1% or less.

Preparation of Inoculation Material and Judgment of Test Results

Each strain to be tested was cultured overnight in an incubator set at 37° C. using Muller-Hinton broth, and the resulting broth was diluted to a density of about $10^6$ cells/1 ml using Muller-Hinton broth. About 5 μl portion of the dilution was inoculated onto the surface of the drug-containing agar medium using a microplanter. The thus inoculated agar plate was cultured at 37° C. for 18 hours in an incubator. After completion of the culturing, the agar plate was observed, and the minimum drug concentration by which cell growth was not observed was defined as MIC.

Results

1-Hydroxy-2-(2-trans-nonenyl)-3-methyl-4(1H)-quinolone showed an MIC value of 12.5 μg/ml or more against typical facultative anaerobes and aerobes such as *Staphylococcus aureus* FDA 209P, *Escherichia coli* 0–1 and *Pseudomonas aeruginosa* NCTC 10490.

EXAMPLE 4

An in vitro test on anaerobes was carried out in the following manner.

Preparation of Antibacterial Substance-containing Agar Plate

The substance to be evaluated was dissolved in 100% dimethyl sulfoxide (DMSO) and diluted by 2-fold serial dilution. Each of the dilution solutions was put into a sterilized round Petri dish and mixed with 10 ml of GAM agar medium which had been sterilized and kept at 50° C., and the mixture was solidified. Final concentration of DMSO becomes 1% or less.

Preparation of Inoculation Material and Judgment of Test Results

Each strain to be tested was cultured overnight at 37° C. in GAM broth using an anaerobic culturing apparatus whose inside atmosphere had been replaced with a mixed gas system of 80% $N_2$, 10% $CO_2$ and 10% $H_2$, and the resulting broth was diluted to a density of about $10^6$ cells/1 ml using the same GAM broth. About 5 μl portion of the dilution was inoculated onto the surface of the drug-containing agar medium using a microplanter. The thus inoculated agar plate was cultured at 37° C. for 18 hours using the anaerobic culturing apparatus. After completion of the culturing, the agar plate was observed, and the minimum drug concentration by which cell growth was not observed was defined as MIC.

Results

1-Hydroxy-2-(2-trans-nonenyl)-3-methyl-4(1H)-quinolone showed an MIC value of larger than 25 μg/ml against typical facultative anaerobes such as *Bifidobacterium bifidum* CAYA 21-1, *Peptostreptococcus productus* CAYA 12-2 and *Bacteroides fragiris* GAI 5562.

EXAMPLE 5

Measurement of in vivo antibacterial activity upon *Helicobacter pylori* was carried out in the following manner.

In vivo Antibacterial Activity

Infection experiment was carried out using Mongolian gerbils on which stable infection has been reported (*J. Gastroenterology*, 31: supple IX, 24–28, 1996). *Helicobacter pylori* ATCC 43504 was cultured overnight in Brucella broth containing 5% calf serum, and the cell suspension was inoculated using a sound into the stomach of each Mongolian gerbil (MGS/Sea, male, 4-week-old) which had been subjected to overnight fasting. Treatment was started about 1 week after the infection, by dissolving the drug to be evaluated in a solvent in the usual way and orally administering it twice a day for 3 days in a dose of 10 mg/kg, 1 mg/kg or 0.1 mg/kg. The stomach was excised and homogenized on the next day after completion of the administration. The stomach homogenate was diluted by 10-fold serial dilution, inoculated onto modified Skirrow's medium and cultured at 37° C. for 6 to 7 days under microaerophilic or 10% $CO_2$ condition. The number of cells in the stomach was calculated from the number of grown colonies. As the result, it was confirmed that 1-hydroxy-2-(2-trans-nonenyl)-3-methyl-4(1H)-quinolone reduces the number of viable cells in the stomach.

What is claimed is:

1. A method of treating a *Helicobacter pylori* infection in a subject which comprises orally administering to a subject in need of treatment, a therapeutically effective amount of a 1-hydroxy-3-methyl-quinolone derivative represented by the formula (I)

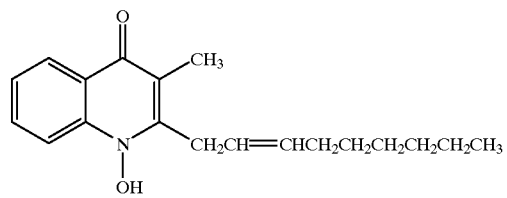

or a pharmaceutically acceptable salt thereof as an active ingredient.

2. The method as claimed in claim 1, wherein said 1-hydroxy-3-methyl-quinolone derivative is 1-hydroxy-2-(2-trans-nonenyl)-3-methyl-4(1H)-quinolone or a pharmaceutically acceptable salt thereof.

3. A method of treating a *Helicobacter pylori* infection in a subject which comprises orally administering to a subject in need of treatment, a therapeutically effective amount of a 1-hydroxy-3-methyl-quinolone derivative represented by the formula (I)

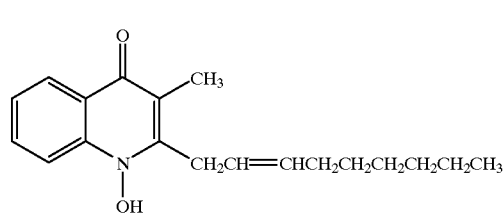

or a pharmaceutically acceptable salt thereof as the sole active ingredient.

4. The method as claimed in claim 3, wherein said 1-hydroxy-3-methyl-quinolone derivative is 1-hydroxy-2-(2-trans-nonenyl)-3-methyl-4(1H)-quinolone or a pharmaceutically acceptable salt thereof.

* * * * *

UNITED STATES PATENT AND TRADEMARK OFFICE
CERTIFICATE OF CORRECTION

PATENT NO.    : 6,184,230 B1
DATED         : February 6, 2001
INVENTOR(S)   : Watanabe, Masato, Tanaka, Kouichi, Komiya, Masayuki, Rantiatmodjo, Ratna Murni It is certified that error appears in the above-identified patent and that said Letters Patent is hereby corrected as shown below:

<u>Title page, item [86],</u>
In §371 Date, please change "November 16, 1999" to -- November 9, 1999 --.
In §102(e) Date, please change "November 16, 1999" to -- November 9, 1999 --.

<u>Column 1,</u>
Line 29, "antitumor" should be changed to -- anti-ulcer --.

Signed and Sealed this

Thirtieth Day of October, 2001

Attest:

*Attesting Officer*

NICHOLAS P. GODICI
*Acting Director of the United States Patent and Trademark Office*